United States Patent [19]
Seltzer et al.

[11] Patent Number: 4,891,424
[45] Date of Patent: Jan. 2, 1990

[54] 4-ARALKYL-2-NITRO-2'-HYDROXY-3',5'-DIALKYL (OR CUMYL)-AZOBENZENES

[75] Inventors: Raymond Seltzer, New City; Roland A. E. Winter, Armonk, both of N.Y.

[73] Assignee: Ciba-Geigy Corporation, Ardsley, N.Y.

[21] Appl. No.: 176,557

[22] Filed: Apr. 1, 1988

Related U.S. Application Data

[62] Division of Ser. No. 772,221, Sep. 3, 1985, Pat. No. 4,760,148.

[51] Int. Cl.$^4$ .................. C07C 107/06; C09D 29/01; C09D 29/12
[52] U.S. Cl. .................... 534/649; 534/558; 534/565; 534/581; 534/582; 534/583; 534/843; 534/887; 564/336; 564/384; 564/392; 568/731; 568/743
[58] Field of Search .................. 534/843, 649

[56] References Cited
U.S. PATENT DOCUMENTS 3,998,804 12/1976 Rody et al. ............. 534/843 X
4,226,763 10/1980 Dexter et al. ........... 534/843 X
4,278,589 7/1981 Dexter et al. ........... 534/843 X
4,347,180 8/1982 Winter et al. ........... 534/843 X Primary Examiner—Floyd D. Higel
Attorney, Agent, or Firm—Luther A. R. Hall

[57] ABSTRACT

4-Aralkyl-2-nitro-2'-hydroxy-3',5'-dialkyl (or cumyl)-azobenzenes are made by coupling the corresponding diazotized 4-aralkyl-o-nitroaniline with the corresponding phenol. These azobenzene intermediates are used to prepare the corresponding 2H-benzotriazole UV absorber stabilizers substituted on the 5-position of the benzo ring by an aralkyl group, preferably alpha,alpha-dimethylbenzyl.

8 Claims, No Drawings

4-ARALKYL-2-NITRO-2'-HYDROXY-3',5'-DIALKYL (OR CUMYL)-AZOBENZENES

This is a divisional of application Ser. No. 772,221, filed on Sept. 3, 1985, now U.S. Pat. No. 4,760,148, issued on July 26, 1988.

BACKGROUND OF THE INVENTION

The present invention relates to selected 2-aryl-2H-benzotriazoles which are useful in protecting light-sensitive organic materials from deterioration and to stabilized compositions containing said benzotriazoles.

The UV absorbers of the o-hydroxyphenyl-2H-benzotriazole class have long been known as effective light stabilizers for organic materials and have enjoyed considerable commercial success.

However, the hitherto known 2-aryl-2H-benzotriazoles of this group have in some circumstances exhibited limited compatibility in certain substrates, and excessive tendency to exude, sublime and/or volatilize during processing of stabilized compositions into sheets, films, fibers or other pellicles when processing must be done at elevated temperatures. Likewise such benzotriazoles may also suffer undue loss by volatilization or sublimation from fabricated structures, particularly thin films or coatings, especially when subjected to elevated temperatures during use.

Attempts have been made to increase substrate compatibility or solubility and to reduce volatilization loss by modifying the structure of the benzotriazoles.

In U.S. Pat. No. 3,230,194, a higher alkyl group was substituted for methyl and the compound 2-(2-hydroxy-5-tert-octylphenyl)-2H-benzotriazole exhibited superior compatibility and performance in polyethylene.

In U.S. Pat. No. 4,127,586, still other modifications to the 2-aryl-2H-benzotriazole moiety were made to increase still further compatibility in substrates and resistance to volatilization. The compound 2-[2-hydroxy-3-(1-phenylethyl)-5-methylphenyl]-2H-benzotriazole described therein exhibited better compatibility and better resistance to loss by volatilization during processing than did the earlier prior art benzotriazole compounds.

In Japanese Kokai 158588/75, other benzotriazole light stabilizers such as 2-(2-hydroxy-3-alpha, alphadimethylbenzyl-5-methylphenyl)-2H-benzotriazole are disclosed.

However, still better resistance to loss from stabilized compositions during high temperature processing remained a practical objective and need in the art for the benzotriazole UV-absorbers.

U.S. Pat. No. 4,226,763 describes attemps to increase the resistance of benzotriazole light absorbers to loss by volatilization. This patent describes 2-(2-hydroxy-3,5-di-alpha-cumylphenyl)-2H-benzotriazole which exhibits superior resistance to loss from stabilized compositions during high temperature processing or in end use applications where coatings or films of the stabilized compositions are exposed even to ambient weathering the light exposures compared to stabilized compositions containing the 2-aryl-2H-benzotriazole of the prior art. This superior performance is attained at the cost of relatively low solubility in some substrates and processing solvents.

U.S. Pat. No. 4,283,327 describes 2-(2-hydroxy-3,5-di-tert-octylphenyl)-2H-benzotriazole which exhibits enhanced solubility in processing solvents and substrates, but which did not have outstanding resistance to loss by volatilization.

U.S. Pat. No. 4,278,589 describes benzotriazoles having one alpha-cumyl group and one tert-octyl substituent on the 2-phenyl moiety in an attempt to achieve a balance of properties not obtained with two alpha-cumyl or with two tert-octyl groups. Benzotriazoles with a good balance of solubility and resistance to loss by volatilization were obtained, but not the outstanding levels of each required by an increasingly demanding market place for light stabilizers with truly exceptional properties.

Although lower alkyl, lower alkoxy and halogen substitution on the benzo ring of 2H-benzotriazole has long been known for example in U.S. Pat. No. 4,127,586, the substitution of the benzo ring with benzyl, alpha-methylbenzyl, alpha, alpha-dimethylbenzyl or other phenylalkyl groups is not known. Japanese Sho 59/172,655 generically discloses such substitution, but specifically only describes aralkyl substitution on the 2-phenyl ring of the 2-aryl-2H-benzotriazole stabilizers.

Traditionally lacquers have been used in the automotive and other industries to produce high gloss coatings. Such lacquers typically consist of high molecular weight polymers dissolved in appropriate solvents. The solvents which usually constitute over 70% of the paint evaporate on baking to leave a polymer film.

Energy and environmental considerations have more recently resulting in development of so called "high solids enamels" as alternate coating systems, which meet government mandated reduction in "volatile organic compounds (VOC)". High solids enamels typically consist of low molecular weight copolymers of methyl methacrylate, hydroxyethyl methacrylate, butyl acrylate and styrene. These copolymers which contain pendant hydroxyl groups are then blended with melamine crosslinking resins (ratios of about 7:3). The final crosslinking reaction occurs when the painted article is subjected to baking. High solids enamels in contrast to lacquers contain usually less than 50% solvent.

The bulk of these solvents are employed during the monomer polymerization process. Only a small quantity of solvent generally less than 10% of the total solvent is retained as "hold out" solvent to be added later to the final point The light stabilizing additives must be soluble enough in this hold out solvent to permit incorporation at this stage. The amount of solvent cannot be changed at will because paint viscosity is a critical parameter in avoiding defects such as runs and sags. To meet these demands for high solubility and instant stabilizers were developed. These products also meet and/or exceed the state of the art materials with respect to compatibility with the resin and lack of volatility.

DETAILED DISCLOSURE

This invention pertains to selected 2-aryl-2H-benzotriazole light absorbers and to organic materials stabilized thereby.

More particularly, the 2-aryl-2H-benzotriazoles of this invention are represented by the formula I

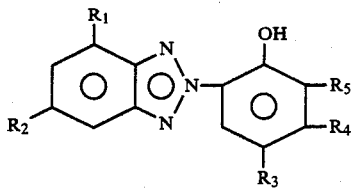

(I)

wherein

R₁ and R₂ are independently hydrogen, halogen, alkyl of 1 to 18 carbon atoms or a group of formula II

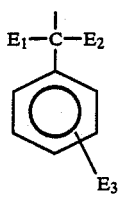

(II)

wherein E₁ and E₂ are independently hydrogen or alkyl of 1 to 4 carbon atoms and E₃ is hydrogen, halogen or alkyl of 1 to 4 carbon atoms, with the proviso that at least one of R₁ and R₂ must be a group of formula II; R₃ is hydrogen, hydroxyl, alkyl of 1 to 12 carbon atoms, alkoxy of 1 to 4 carbon atoms, phenyl, phenyl substituted by one, two or three alkyl groups having 1 to 8 carbon atoms, cycloalkyl of 5 to 6 carbon atoms, carboalkoxy of 2 to 9 carbon atoms, chlorine, carboxyethyl or a group of formula II, R₄ is hydrogen, alkyl of 1 to 4 carbon atoms, alkoxy of 1 to 12 carbon atoms, chlorine or hydroxyl, and R₅ is hydrogen, hydroxyl, alkyl of 1 to 12 carbon atoms, chlorine, cycloalkyl of 5 to 6 carbon atoms or a group of formula II;

with the proviso that R₃, R₄ and R₅ cannot each be hydrogen at the same time, and that only one of R₃, R₄ and R₅ can be hydroxy at the same time.

When R₁, R₂ or E₃ is halogen, it may be fluorine, bromine, chlorine or iodine, preferably chlorine.

When R₁ or R₂ is alkyl or 1 to 18 carbon atoms, it may be for example methyl, ethyl, n-propyl, isopropyl, n-butyl, sec-butyl, isobutyl, tert-butyl, tert-amyl, 2-ethylhexyl, n-octyl, tert-octyl, n-dodecyl, tert-dodecyl or n-octadecyl.

When E₁, E₂ or E₃ is alkyl of 1 to 4 carbon atoms, it is for example methyl, ethyl, n-propyl, isopropyl, n-butyl or tert-butyl.

When E₃ is halogen, it may be fluorine, bromine, chlorine or iodine, preferably chlorine.

R₃ can be alkyl of 1 to 12 carbon atoms such as methyl, ethyl, sec-butyl, tert-butyl, tert-amyl, tert-octyl or n-dodecyl. R₃ can also be alkoxy of 1 to 4 carbon atoms such as methoxy, ethoxy or n-butoxy. R₃ is also phenyl substituted with one, two or three alkyl groups, said alkyl group having 1 to 8 carbon atoms such as methyl, tert-butyl, tert-amyl or tert-octyl. R₃ can also be cycloalkyl of 5 to 6 carbon atoms such as cyclopentyl or cyclohexyl. R₃ is also carboalkoxy of 2 to 9 carbon atoms such as carbomethoxy, carboethoxy, carbo-n-butoxy or carbo-n-octoxy. R₃ is also a group of formula II such as benzyl, alpha-methylbenzyl or alpha, alpha-dimethylbenzyl(=alpha-cumyl).

R₄ can be lower alkyl of 1 to 4 carbon atoms such as methyl, ethyl or n-butyl.

R₄ can also be alkoxy of 1 to 12 carbon atoms such as methoxy, ethoxy, n-butyloxy, octyloxy or dodecyloxy.

R₅ can be alkyl or 1 to 12 carbon atoms such as methyl, sec-butyl, tert-butyl, tert-amyl, tert-octyl, n-dodecyl or tert-dodecyl.

R₅ can also be cycloalkyl or 5 to 6 carbon atoms such as cyclopentyl or cyclohexyl. R₅ is also a group of formula II such as benzyl, alpha-methylbenxyl or alpha, alpha-dimethylbenzyl.

Preferred compounds are those where only one of R₁ and R₂ is a group of formula II and most preferred are those where R₁ is hydrogen and R₂ is a group of formula II.

Still more preferred are the compounds where R₁ is hydrogen, R₂ is a group of formula II where at least one of E₁ and E₂ is methyl and where E₃ is hydrogen or alkyl of 1 to 4 carbon atoms, especially hydrogen or p-methyl. R₂ is most especially alpha, alpha-dimethylbenzyl.

Preferably R₃ is alkyl of 1 to 8 carbon atoms, or a group of formula II.

Preferably R₄ is hydrogen, hydroxyl, methyl, or alkoxy of 1 to 8 carbon atoms.

Preferably R₅ is hydrogen, alkyl of 1 to 8 carbon atoms or a group of formula II.

Most preferably R₃ is methyl, tert-butyl, tert-amyl, tert-octyl, sec-butyl, benzyl, alpha-methylbenzyl or alpha, alpha-dimethylbenzyl.

Most preferably R₄ is hydrogen.

Most preferably R₅ is hydrogen, methyl, sec-butyl, tert-butyl, tert-amyl, tert-octyl, benzyl, alpha-benzyl, or alpha, alpha-dimethylbenzyl.

SYNTHESIS OF COMPOUNDS

The compounds of this invention are prepared the manner set forth in U.S. Pat. No. 4,226,763 wherein the substituted 2-nitroaniline is diazotized and then coupled, preferably in a strongly alkaline medium, with the appropriate phenol to give the intermediate o-nitroazobenzene.

This o-nitroazobenzene intermediate is converted to the corresponding 2-aryl-2-H-benzotriazole by reductive cyclization using any number of conventional reducing systems including zinc and alkali, hydrazine, catalytic hydrogenation, and the like.

Many of the various starting materials such as the substituted phenols, o-nitroaniline, alpha-methylstyrene, 5-chloro-2-nitroaniline, styrene, benzyl alcohol, and the like are items of commerce or can easily be prepared by known methods.

The substituted phenols are conveniently made by the alkylation of phenol with an olefin in the presence of an acidic catalyst. The preparation of 2,4-di(alpha, alphadimethylbenzyl)phenol, described in U.S. Pat. No. 4,226,763, is a typical illustration.

The substituted o-nitroanilines required to obtain the instant compounds substituted on the benzo ring with benzyl, alpha-methylbenzyl or alpha-cumyl (=alpha, alphadimethylbenzyl) groups can be prepared by the aralkylation of an o-nitroaniline using for example an olefin (such as styrene or alpha-methylstyrene), an alcohol (such as benzyl alcohol) or an ester (such as alpha-cumyl acetate) in the presence of an acidic catalyst.

The o-nitroazobenzene intermediates of formula III

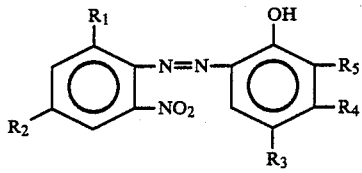

(III)

where $R_1$, $R_2$, $R_3$, $R_4$ and $R_5$ are defined above are also new compounds and are part of this invention.

The compounds of this invention are effective light stabilizers in a wide range of organic polymers. Polymers which can be stabilized include:

1. Polymers which are derived from mono- or diolefins, e.g., polyethylene which can optionally be cross-linked, polypropylene, polyisobutylene, polymethylbutene-1, polymethylpentene-1, polyisoprene, polybutadiene.

2. Mixtures of the homopolymers cited under 1), for example mixtures of polypropylene and polyethylene, polypropylene and polybutene-1, polypropylene and polyisobutylene.

3. Copolymers of the monomers based on the homopolymers cited under 1), for example ethylene/propylene copolymers, propylene/butene-1 copolymers, propylene/isobutylene copolymers, ethylene/butene-1 copolymers as well as terpolymers of ethylene and propylene with a diene, for example hexadiene, dicyclopentadiene or ethylidene norbornene, and copolymers of α-olefins, e.g., ethylene with acrylic or methacrylic acid.

4. Polystyrene.

5. Copolymers of styrene and of α-methylstyrene, for example styrene/butadiene copolymers, styrene/acrylonitrile copolymers, styrene/acrylonitrile/methacrylate copolymers, styrene/acrylonitrile copolymers modified with acrylic ester polymers to provide impact strength as well as block copolymers, e.g., styrene/-butadiene/styrene block copolymers.

6. Graft copolymers of styrene, for example the graft polymer of styrene to polybutadiene, the graft polymer of styrene with acrylonitrile to polybutadiene as well as mixtures thereof with the copolymers cited under 5), commonly referred to as acrylonitrile/butadiene/styrene or ABS plastics.

7. Halogen-containing vinyl polymers, for example polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, vinylidene chloride/vinyl acetate copolymers.

8. Polymers which are derived from α,β-unsaturated acids and derivatives thereof, polyacrylates and polymethacrylates, polyacrylic amides and polyacrylonitrile. The instant compounds are advantageously used in heat-curable acrylic resin lacquers which are composed of a copolymer of acrylic acid and one or more of its derivatives, and a melamine-formaldehyde resin.

9. Polymers which are derived from unsaturated alcohols and amines and from the acyl derivatives thereof or acetals, for example polyvinyl alcohol, polyvinyl acetate, polyvinyl stearate, polyvinyl benzoate, polyvinyl maleate, polyvinyl butyral, polyallyl phthalate, polyallyl melamine and copolymers thereof with other vinyl compounds, for example ethylene/vinyl acetate copolymers.

10. Homopolymers and copolymers which are derived from epoxides, for example polyethylene oxide or the polymers which are derived from bis-glycidyl ethers.

11. Polyacetals, for example polyoxymethylene, as well as polyoxymethylenes which contain ethylene oxide as comonomer.

12. Polyalkylene oxides, for example polyoxyethylene, polypropylene oxide or polyisobutylene oxide.

13. Polyphenylene oxides.

14. Polyurethanes and polyureas, such as in urethane coatings.

15. Polycarbonates.

16. Polysulfones.

17. Polyamides and copolyamides which are derived from diamines and dicarboxylic acids and/or from aminocarboxylic acids or the corresponding lactams, for example polyamide 6, polyamide 6/6, polyamide 6/10, polyamide 11, polyamide 12, poly-m-phenylene-isophthalamide.

18. Polyesters which are derived form dicarboxylic acids and dialcohols and/or from hydroxycarboxylic acids or the corresponding lactones, for example polyethylene glycol terephthalate, poly-1,4-dimethylolcyclohexane terephthalate.

19. Cross-linked polymers which are derived from aldehydes on the one hand and from phenols, ureas and melamine on the other, for example phenol/formaldehyde, urea/formaldehyde and melamine/formaldehyde resins.

20. Alkyd resins, for example glycerol/phthalic acid resins and mixtures thereof with melamine/formaldehyde resins.

21. Unsaturated polyesters resins which are derived from copolyesters of saturated and unsaturated dicarboxylic acids with polyhydric alcohols as well as from vinyl compounds as cross-linking agents and also the halogen-containing, flame-resistant modifications thereof.

22. Natural polymers, for example cellulose, rubber, as well as the chemically modified homologous derivatives thereof, for example cellulose acetates, cellulose propionates and cellulose butyrates and the cellulose ethers, for example methyl cellulose.

While compounds of this invention are very effective stabilizers for a host of organic substrates subject to light induced deterioration, as are the 2-aryl-2H-benzotriazole light absorbers in general, the instant compounds with their surprising resistance to loss from a stabilized composition during high temperature processing due to volatilization, exudation or sublimation have particular value in stabilizing polymeric substrated which are perforce processed at elevated temperatures.

Thus, the compounds of this invention are particularly useful as stabilizers for the protection of polyesters, for instance poly(ethylene terephthalate), poly(butylene terephthalate) or copolymers thereof; of polycarbonates, for example polycarbonate derived from bisphenol A and phosgene, or copolymers thereof; of polysulfones; of polyamides such as nylon-6, nylon-6,6, nylon 6,10 and the like as well as copolyamides; of thermoset acrylic resins; of thermoplastic acrylic resins; of polyolefins such as polyethylene, polypropylene, copolyolefins and the like; and of any polymer system requiring high temperature processing and fabrication.

Although the compounds of the invention may be used above to provide a light stabilizing function, the compounds of this invention are often combined with other stabilizers, even other light stabilizerss, in the preparation of stabilized compositions. The stabilizers may be used with phenolic antioxidants, pigments, colorants or dyes, light stabilizers such as hindered amines, metal deactivators, etc.

In general, the stabilizers of this invention are employed from about 0.1 to about 5% by weight of the stabilized composition, although this will vary with the particular substrate and application. An advantageous range is from about 0.5 to about 3%.

The stabilizers of Formula I may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain from about 0.1 to about 5%, preferably from about 0.5 to about 3% by weight of various conventional additives, such as the following, particularly phenolic antioxidants or light-stabilizers, or mixtures thereof:

1. Antioxidants 1.1 Simple 2,6-dialkylphenols, such as, for example, 2,6-ditert.-butyl-4-methylphenol, 2-tert.-butyl-4,6-dimethylphenol, 2,6di-tert.-butyl-4-methoxymethylphenol and 2,6-dioctadecyl-4-methylphenol.

1.2 Derivatives of alkylated hydroquinones, such as for example, 2,5-di-tert.-butyl-hydroquinone, 2,5-di-tert.-amyl-hydroquinone, 2,6-di-tert.-butyl-hydroquinone, 2,5-di-tert.-butyl-4-hydroxy-anisole, 3,5-di-tert.-butyl-4-hydroxy-anisole, 3,5-di-tert.-butyl-4-hydroxyphenyl stearate and bis-(3,5-di-tert.-butyl-4-hydroxyphenyl) adipate.

1.3 Hydroxylated thiodiphenyl ethers, such as for example, 2,2'-thio-bis-(6-tert.-butyl-4-methylphenol), 2,2'-thio-bis-(4-octylphenol), 4,4'-thio-bis-(6-tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxyphenyl) disulfide.

1.4 Alkylidene-bisphenols, such as, for example, 2,2'-methylene-bis-(6-tert.-butyl-4-methylphenol), 2,2'-methylene-bis-(6-tert.-butyl-4-ethylphenol), 4,4'-methylene-bis-(6tert.-butyl-2-methylphenol, 4,4'-methylene-bis-(2,6-di-tert.-butyl-phenol), 2,6-di(3-tert.-butyl-5-methyl-2-hydroxybenzyl)-4-methylphenol, 2,2'-methylene-bis-[4-methyl-6-(α-methylcyclohexyl)-phenol], 1,1-bis(3,5-dimethyl-2-hydroxyphenyl)-butane, 1,1-bis-(5-tert.-butyl-4-hydroxy-2-methylphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis-(5-tert.-butyl-4-hydroxy-2-methylphenyl)-4-n-dodecylmercapto-butane, 1,1,5,5-tetra-(5-tert.-butyl-4-hydroxy-2-methylphenyl)-pentane and ethylene glycol bis-[3,3-bis-(3-tert.-butyl-4-hydroxyphenyl)-butyrate].

1.5 O-, N- and S-benzyl compounds, such as for example, 3,5,3',5'-tetra-tert.-butyl-4,4'-dihydroxydibenzyl ether, octadecyl 4-hydroxy-3,5-dimethylbenzyl-mercaptoacetate, tris-(3,5-di-tert.-butyl-4-hydroxybenzyl)-amine and bis-(4-tert.-butyl-3-hydroxy-2,6-dimethyl-benzyl) dithioterephthalate.

1.6 Hydroxybenzylated malonates, such as for example, dioctadecyl 2,2-bis-(3,5-di-tert.-butyl-2-hydroxybenzyl)-malonate, dioctadecyl 2-(3-tert.-butyl-4-hydroxy-5-methylbenzyl)-malonate, di-dodecylmercapto-ethyl 2,2-bis-(3,5-di-tert.-butyl-4-hydroxybenzyl)-malonate and di-[4-(1,1,3,3-tetramethylbutyl)-phenyl] 2,2-bis-(3,5di-tert.-butyl-4-hydroxybenzyl)-malonate.

1.7 Hydroxybenzyl-aromatic compounds, such as, for example, 1,3,5tri-(3,5-di-tert.-butyl-4-hydroxybenzyl)-2,4,6-trimethylbenzene, 1,4-di-(3,5-di-tert-butyl-4-hydroxybenzyl)-2,3,5,6-tetramethylbenzene and 2,4,6-tri-(3,5-di-tert.-butyl-4-hydroxybenzyl)-phenol.

1.8 s-Triazine compounds, such as, for example 2,4-bisoctylmercapto-6-(3,5-di-tert.-butyl-4-hydroxyanilino)-s-triazine, 2-octylmercapto-4,6-bis-(3,5-di-tert.-butyl-4-hydroxyanilino)-s-triazine, 2-octylmercapto-4,6-bis-(3,5-di-tert.-butyl-4-hydroxyphenoxy)-s-triazine, 2,4,6-tris-(3,5-di-tert.-butyl-4-hydroxyphenoxy)-s-triazine, 2,4,6-tris-(3,5-di-tert-butyl-4-hydroxyphenylethyl)-s-triazine and 1,3,5-tris-(3,5-di-tert.-butyl-4-hydroxybenzyl)isocyanurate.

1.9 Amides of β-(3,5-di-tert.-butyl-4-hydroxyphenyl)-propionic acid, such as, for example, 1,3,5-tris-(3,5,-di-tert.-butyl-4-hydroxyphenyl-propionyl)-hexahydro-s-triazine and N,N'-di-3,5-di-tert.-butyl-4-hydroxyphenyl-propionyl)-hexamethylenediamine, N,N'-bis-β-(3,5-di-t-butyl-4-hydroxyphenyl)-propionyl-hydrazine.

1.10 Esters of β-(3,5-di-tert.-butyl-4-hydroxyphenyl)-propionic acid with monohydric or polyhydric alcohols, such as for example, with methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thiaundecanol, 3-thia-pentadecanol, trimethylhexnediol, trimethylolethane, trimethylolpropane, tris-hydroxyethyl isocyanurate and 4-hydroxymethyl-1-phospha-2,6,7-trioxabicyclo-[2.2.2]octane.

1.11 Esters of β-(5tert.-butyl-4-hydroxy-3-methylphenyl-propionic acid with monohydric or polyhydric alcohols, such as for example, with methanol, ethanol, octadecanol, 1,6-hexanediol, 1.9-nonanediol, ethylene glycol, 1,2-propanediol, diethylene glycol, thiodiethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2.2.2]octane.

1.12 Esters of 3,5-di-tert.-butyl-4-hydroxyphenylacetic acid with monohydric or polyhydric alcohols, such as for example, with methanol, ethanol, octadecanol, 1,6-hexandiol, 1,9-nonanediol, ethylene glycol, 1,2-propenediol, diethylene glycol, thio-diethylene glycol, neopentylglycol, pentaerythritol, 3-thiaundecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2.2.2]-octane especially the tetrakis ester of pentaerythritol.

1.13 Benzylphosphonates, such as, for example, dimethyl 3,5 di-tert.-butyl-4-hydroxybenzylphosphonate, diethyl 3,5-di-tert.-butyl-4-hydroxybenzylphosphonate, dioctadecyl 3,5-di-tert.-butyl-4-hydroxybenzylphosphonate and dioctadecyl 5-tert.-butyl-4-hydroxy-3-methylbenzylphosphonate.

2. Light-stabilizers 2.1 Esters of optionally substituted benzoic acids, e.g., 3,5-di-tert.-butyl-4-hydroxybenzoic acid, 2,4-di-tert.-butylphenyl ester or -octadecyl ester or 2-methyl-4,6-di-tert.-butylphenyl ester.

2.2 Sterically hindered amines, e.g., 4-benzoyl-2,2,6,6-tetramethylpiperidine, 4-stearyloxy-2,2,6,6-tetramethylpiperidine, bis-(2,2,6,6-tetramethylpiperidyl) sebacate, bis-(1,2,2,6,6-pentamethylpiperidyl) 2-n-butyl-2-(2-hydroxy-3,5-di-tert-butylbenzyl)malonate or 3-n- octyl-7,7,9,9-trimethyl-1,3,8-triazaspiro[4.5]decane-2,4-dione.

2.3 Oxalic acid diamides, e.g., 4,4'-di-octyloxy-oxanilide, 2,2'-di-octyloxy-5,5'-di-tert.-butyl-oxanilide, 2,2'-di-dodecyloxy-5,5'-di-tert.-butyl-oxanilide, 2-ethoxy-2'-ethyl-oxanilide, N,N'-bis-(3-dimethyl-aminopropyl)-oxalamide, 2-ethoxy-5-tert.-butyl-2'-ethyl-oxanilide and the mixture thereof with 2-ethoxy-2'-ethyl-5,4'-di-tert.-butyl-oxanilide, or mixtures of ortho- and paramethoxy- as well as of o- and p-ethoxy-disubstituted oxanilides.

3. Metal deactivators, e.g., oxanilide, isophthalic acid dihydrazide, sebacic acid-bis-phenylhydrazide, bis-benzylideneoxalic acid dihydrazide, N,N'-diacetal-adipic acid dihydrazide, N,N'-bis-salicyloyl-oxalic acid dihydrazide, N,N'-bis-salicyloylhydrazine, N,N'-bis-(3,5-di-tert.-butyl-4-hydroxyphenylpropionyl)-hydrazine, N-salicyloyl-N'-salicylalhydrazine, 3-salicyloyl-amino-1,2-4-triazole or N,N'-bis-salicyloyl-thiopropionic acid dihydrazide.

4. Basic co-stabilizers, e.g., alkali metal salts and alkaline-earth metal salts of higher fatty acids, for example Ca-stearate, Zn-stearate, Mg-behenate, Na-ricinoleate or K-palmitate.

5. Nucleation agents, e.g., 4-tert.-butylbenzoic acid, adipic acid or diphenylacetic acid.

6. Phosphites and phosphonites, such as, for example, triphenyl phosphite, diphenylalkyl phosphites, phenyldialkyl phosphites, tri-(nonyl-phenyl) phosphite, trilauryl phosphite, trioctadecyl phosphite and 3,9-isodecyloxy-2,4,8,10-tetraoxa-3,9-diphospha-[5.5]-undecane and tetra(2,4-di-tert-butylphenyl) diphenylene-4,4'-bis(phosphonite).

Other additives that can be incorporated in the stabilized compositions are thiosynergists such as dilauryl thiodiproprionate, lubricants such as stearyl alcohol, fillers, asbestos, kaolin, talc, glass fibers, pigments, optical brighteners, flameproofing agents and antistatic agents.

The following examples are presented for the purpose of illustration only and are not to be construed to limit the nature or scope of the instant invention in any manner whatsoever.

Example 1

4-alpha-Cumyl-2-nitroaniline

In a 12-liter reaction flask fitted with a condenser, nitrogen inlet, stirrer, thermometer and addition funnel is placed 187.4 grams (1.375 moles) of anhydrous zinc chloride. The flask is placed under a nitrogen atmosphere and 459 ml (5.5 moles) of concentrated (12N) hydrochloric acid is added over a 10-minute period with the temperature rinsing from 22° to 40° C. To this is then added 760 grams (5.5 moles) of o-nitroaniline over a 15-minute period to avoid the formation of lumps. The resulting thick red slurry is heated to 60° C. and then 858 ml (6.6 moles) of alpha-methylstyrene is added gradually over a 110-minute period with the temperature rising during this period from 60° to 90° C. The deep red fluid reaction mixture is heated for another 200 minutes at 90°–105° C. till only a trace of o-nitroaniline is observed by thin layer chromatography.

The hot reaction mixture is diluted with 3 liters of toluene and stirred. The aqueous phase is separated at 60° C. and the toluene phase is washed with 4×700 ml of water. The toluene phase is filtered and the filtrate is dried over anhydrous sodium sulfate. The dry toluene solution is heated to 70° C. and 4 liters of heptane are added in 1-liter portions keeping the temperature above 55° C. The mixture is then cooled to give 4-alpha-cumyl-2-nitroaniline as red-orange crystals in a yield of 976 grams (69.2%), melting at 92°–94° C.

EXAMPLE 2

4-alpha-Methylbenzyl-2-nitroaniline

When an equivalent amount of styrene is substituted for alpha-methylstyrene in the procedure of Example 1, 4-alpha-methylbenzyl-2-nitroaniline is obtained as crystals, melting at 95.5°–97° C.

EXAMPLE 3

4-Benzyl-2-nitroaniline

When an equivalent amount of benzyl alcohol is substituted for alpha-methylstyrene in the procedure of Example 1, 4-benzyl-2-nitroaniline is obtained.

EXAMPLE 4

2,4-Di-(alpha,alpha-dimethylbenzyl)phenol

This intermediate is made by reacting a mixture of 705.8 grams (7.5 moles) of phenol with 1772.7 grams (15 moles) of alpha-methylstyrene in the presence of 25.7 grams (0.135 moles) of P-toluenesulfonic acid monohydrate catalyst. This mixture is heated under nitrogen at 140° C. for 2.5 hours. The reaction mixture is cooled at 110° C. and 1125 ml of toluene is added. After washing the resulting solution at 80° C. with 750 ml of an aqueous solution of 37.5 grams of sodium carbonate and 75 grams of sodium chloride, the organic phase is washed thrice with 1000 ml of aqueous sodium chloride solution; then dried over anhydrous sodium sulfate; filtered and vacuum distilled. The above-named product is obtained as the main fraction boiling at 172°–175° C./0.15–0.18 mm Hg in a yield of 1229.8 grams (49.6% of theory). The product melts at 63°–65° C.

EXAMPLE 5

4-alpha,alpha-Dimethylbenzyl-2-nitrobenzene Diazonium Chloride

In a 500-ml flask fitted with a stirrer and thermometer, 76.9 grams (0.3 mole) of 4-alpha,alpha-dimethylbenzyl-2-nitroaniline is suspended in 200 ml of xylene. To this is added at 25° C. 86.4 grams (0.9 mole) of concentrated hydrochloric acid. The suspension is stirred at 38° C. for 1 hour followed by the addition of 60 ml of water. The mixture is cooled to 20° C. and seeded upon which the corresponding hydrochloride salt crystallized as a granular precipitate. The mixture is cooled to −5° C. and diazotized by the addition over a period of 30 minutes of 21.4 grams (0.31 mole) of solid sodium nitrite keeping the temperature at −5° C. to −2° C. The mixture is stirred at −2° C. for 1 hour. Two phases occur and are separated. The lower aqueous phase contains the desired diazonium chloride and has a weight of 244.1 grams and corresponds to 0.3 mole of diazonium chloride solution.

EXAMPLE 6

4-alpha,alpha-Dimethylbenzyl-2-nitro-2'-hydroxy-3',5'-di-tert-butylazobenzene In a 1-liter flask, 54 grams (1.35 moles) of sodium hydroxide pellets are dissoled in 500 ml of methanol. To this is added 51.6 grams (0.25 mole) of 2,4-di-tert-butylphenol and 50 ml of xylene. The resulting solution is cooled to −8° C. Over a period of 6 hours is added 244 grams (0.3 mole) of the diazonium chloride solution, prepared in Example 5, keeping the temperature at −8° C. After stirring overnight, the pH of the reaction mixture is brought to 9 by the addition of 55 ml (0.68 mole) of concentrated hydrochloric acid.

The supernatant liquid is removed from the semisolid residue which is the crude azobenzene product which is thrice slurred with 100 ml portions of methanol and then thrice with 100 ml portions of water to remove inorganic salts. The resulting solid precipitate is treated with 300 ml of methanol causing it to crystallize. After filtration at 15° C., the azobenzene product is obtained in a yield of 82.8 grams (69.9%) as a brick-red solid. The product after recrystallization from ethanol melts at 105°–107° C.

EXAMPLE 7

5-alpha,alpha-Dimethylbenzyl-2-(2-hydroxy-3,5-di-tert-burylphenyl)-2-H-benzotriazole To a 1-liter 3-necked flask fitted with a stirrer, thermometer, reflux condenser and nitrogen inlet is charged 101.5 grams (0.214 mol) of the o-nitroazobenzene intermediate of Example 6 and 430 ml of toluene. To the resulting solution is added 64.2 ml of isopropanol and 64.2 ml of water. A nitrogen atmosphere is imposed and 34.2 grams (0.43 mole) of 50% aqueous sodium hydroxide is added. A flask containing 49.2 grams (0.75 gram-atoms) of zinc is connected to the reaction flask by Gooch rubber tubing and the zinc dust is added portionwise to the reaction mixture in seven (7) equal portions with 30 minute intervals between additions. After all the zinc is added, the mixture is stirred at 50° C. overnight and then heated to 75°–80° C. for two hours. The mixture is then cooled to 45° C. and acidified with 214 grams of 50% aqueous sulfuric acid.

The zinc sludge is removed by filtration. The product is contained in the organic layer, which is washed with five 30 ml portions of 70% sulfuric acid, and then dried over anhydrous magnesium sulfate. The toluene solution is concentrated to 150 grams and then diluted with 200 ml of ethanol and seeded to give the above-named product as a white solid in a yield of 52.5 grams (55.6%) melting at 93°–95° C.

Analysis: Calcd for $C_{29}H_{35}N_3O$: C, 78.87; H, 7.99; N, 9.52. Found: C, 78.5; H, 8.2; N, 9.4.

EXAMPLES 8–9

When in the general procedure of Example 5, an equivalent amount of 4-alpha-methylbenzyl-2-nitroaniline (Example 8) or 4-benzyl-2-nitroaniline (Example 9) is substituted for 4-alpha, alpha-dimethylbenzyl-2-nitroaniline, the corresponding diazonium chloride solution is prepared.

EXAMPLES 10–20 o-Nitroazobenzene Intermediates

Using the general procedure of Example 6, the following o-nitroazobenzene intermediates are prepared by selecting the appropriate diazonium chloride solution and the appropriate phenol.

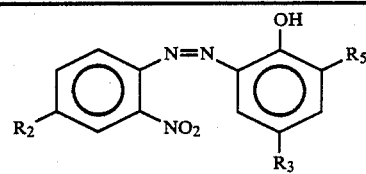

| Example | $R_2$ | $R_3$ | $R_5$ |
|---------|-------|-------|-------|
| 10 | alpha-cumyl* | alpha-cumyl | alpha-cumyl |
| 11 | alpha-cumyl* | tert-octyl | alpha-cumyl |
| 12 | alpha-cumyl* | tert-amyl | tert-amyl |
| 13 | alpha-cumyl* | tert-octyl | tert-octyl |
| 14 | alpha-methylbenzyl** | alpha-cumyl | alpha-cumyl |
| 15 | benzyl*** | alpha-cumyl | alpha-cumyl |
| 16 | alpha-cumyl* | methyl | hydrogen |
| 17 | alpha-cumyl* | tert-octyl | hydrogen |
| 18 | alpha-cumyl* | alpha-cumyl | tert-octyl |
| 19 | alpha-cumyl* | methyl | tert-butyl |
| 20 | alpha-cumyl* | tert-butyl | hydrogen |

*from diazonium chloride of Example 5
**from diazonium chloride of Example 8
***from diazonium chloride of Example 9

EXAMPLE 21

5-alpha,alpha-Dimethylbenzyl-2-[2-hydroxy-3,5-di-(alpha, alpha-dimethylbenzyl)phenyl]-2H-benzotriazole Using the general procedure of Example 7 and the o-nitroazobenzene intermediate of Example 10, the above-named product is obtained in a yield of 59.9% as a white solid melting at 141–142° C.

Analysis: Calcd for $C_{39}H_{39}N_3O$: C, 82.79; H, 6.95; N, 7.43. Found: C, 82.9; H, 7.2; N, 7.5.

The product of Example 21 is obtained in two different crystalline modification forms one of which melts at 114°–116° C. and exhibits far greater solubility in many organic solvents, including xylene and methyl amyl ketone, than the other crystalline form.

EXAMPLE 22

5-alpha,alpha-Dimethylbenzyl-2-(2-hydroxy-3-alpha,alphadimethylbenzyl-5-tert-octylphenyl)-2-H-benzotriazole Using the general procedure of Example 7 and the o-nitroazobenzene intermediate of Example 11, the above named product is obtained in a 34% yield as an amber glass which is recrystallized to a solid melting at 99°–100° C.

Analysis: Calcd for $C_{38}H_{45}N_3O$: C, 81.53; H, 8.10; N, 7.51. Found: C, 81.3; H, 8.3; N, 7.5.

EXAMPLE 23

5-alpha,alpha-Dimethylbenzyl-2-(2-hydroxy-3,5-di-tertamylphenyl-2H-benzotriazole Using the general procedure of Example 7 and the o-nitroazobenzene intermediate of Example 12, the above-named product is obtained in a 34% yield as an amber glass.

Analysis: Calcd for $C_{31}H_{39}N_3O$: C, 79.27; H, 8.37; N, 8.95. Found: C, 80.2; H, 8.5; N, 8.9.

EXAMPLE 24

5-alpha,alpha-Dimethylbenzyl-2-(2-hydroxy-3,5-di-tertoctylphenyl)-2H-benzotriazole Using the general procedure of Example 7 and the o-nitroazobenzene intermediate of Example 13, the above-named product is obtained as a solid, recrystallized from isopropanol, melting at 120°–122° C.

Analysis: Calcd for $C_{37}H_{51}N_3O$: C, 80.24; H, 9.28; N, 7.59. Found: C, 80.3; H, 9.3; N, 7.7.

EXAMPLE 25

5-alpha-Methylbenzyl-2-[2-hydroxy-3,5-di-(alpha,alphadimethylbenzyl)phenyl]-2H-benzotriazole Using the general procedure of Example 7 and the o-nitroazobenzene intermediate of Example 14, the above-named compound is obtained in a yield of 44.4% as a solid melting at 123°–125° C.

Analysis: Calcd for $C_{38}H_{37}N_3O$: C, 82.72; H, 6.76; N, 7.62. Found: C, 82.6; H, 6.7; N, 7.6.

EXAMPLE 26

5-Benzyl-2-[2-hydroxy-3,5-di-(alpha,alpha-dimethylbenzyl)-phenyl]-2H-benzotriazole Using the general procedure of Example 7 and the o-nitroazobenzene intermediate of Example 15, the above-named product is obtained in a yield of 44.6% as a white solid melting at 91°–93° C.

Analysis: Calcd for $C_{37}H_{35}N_3O$: C, 82.65; H, 6.56; N, 7.82. Found: C, 82.5; H, 6.4; N, 7.8.

EXAMPLE 27

5-alpha,alpha-Dimethylbenzyl-2-(2-hydroxy-3-tert-butyl-5-methylphenyl)-2H-benzotriazole Using the general procedure of Example 7 and the o-nitroazobenzene intermediate of Example 19, the above-named compound is obtained as a solid melting at 87°–89° C.

Analysis: Calcd for $C_{26}H_{29}N_3O$; C, 78.16; H, 7.32; N, 10.52. Found: C, 77.9; H, 7.5; N, 10.3.

EXAMPLES 28–31

Using the general procedure of Example 7 and the appropriate o-nitroazobenzene intermediates of Examples 16–18, and 20, the following 2H-benzotriazoles are prepared.

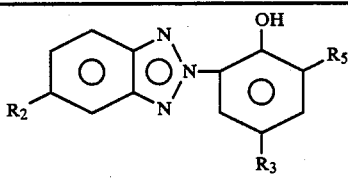

| Example | R₂ | R₃ | R₅ |
|---|---|---|---|
| 28 | alpha-cumyl | methyl | hydrogen |
| 29 | alpha-cumyl | tert-octyl | hydrogen |
| 30 | alpha-cumyl | alpha-cumyl | tert-octyl |
| 31 | alpha-cumyl | tert-butyl | hydrogen |

EXAMPLE 32

Resistance to Loss of Benzotriazole Stabilizers

A number of 2-aryl-2H-benzotriazole light stabilizers are subjected to thermal gravimetric analysis with a flow rate of 100 ml nitrogen/minute both isothermally at 280° C. to indicate the time in minutes to reach 50% weight loss of the stabilizer as well as in a scanning mode at a heating rate of 10°(C.) per minute to ascertain the temperature at which 10% and 50% weight loss of stabilizer are observed.

Experimental data are given on the table which follows.

These results correlate closely with the resistance of the indicated stabilizer to exudation or volatilization during any processing step with polymer formulations during the preparation of sheet, film, fiber or other fabricated pellicles. The absence or essential absence of exuded or volatilized stabilizer on processing equipment (i.e., rollers, guides, orifices, and the like) increases significantly the times between required shut-downs of continuously operated process equipment and represents enormous practical and economic savings related to the specific stabilizer used.

| | TGA Data | | |
|---|---|---|---|
| | Isothermal at 280° C. Time (minutes) to Indicated Weight Loss of Stabilizer | Scanning (at 10° (C.) per minute Temperature °C. to Indicated Weight Loss of Stabilizer | |
| | 50% | 10% | 50% |
| Stabilizer* | | | |
| A | 0.75 | 182 | 215 |
| B | 0.9 | 200 | 233 |
| C | 1.0 | 210 | 247 |
| D | 1.9 | 225 | 260 |
| E | 3.0 | 250 | 290 |
| F | 24 | 300 | 340 |
| G | 7.4 | 267 | 307 |
| of Example | | | |
| 7 | 19 | 295 | 338 |
| 21 | 2040 | 365 | 412 |
| 22 | 840 | 340 | 387 |
| 23 | 33 | 285 | 325 |
| 24 | 40 | 308 | 348 |
| 26 | 3780 | 360 | 405 |

A is 2-(2-hydroxy-5-methylphenyl)-2H—benzotriazole.
B is 2-(2-hydroxy-3,5-di-tert-amylphenyl)-2H—benzo-triazole.
C is 2-(2-hydroxy-3-tert-butyl-5-sec-butylphenyl)-2H—benzotriazole.
D is 2-(2-hydroxy-5-tert-octylphenyl)-2H—benzotriazole.
E is 2-[2-hydroxy-3-(1-phenylethyl)-5-methylphenyl]-2H—benzotriazole.
F is 2-[2-hydroxy-3,5-di-(alpha,alpha-dimethylbenzyl)phenyl]-2H—benzotriazole.
G is 2-[2-hydroxy-3-(alpha,alpha-dimethylbenzyl)-5-tert-octylphenyl]-2H—benzotriazole.

While prior art benzotriazole F exhibits thermogravimetric properties similar to the benzotriazole of Example 7, the benzotriazoles of Examples 21–24 and 26, particularly Examples 21 and 26, are very much more resistant to thermogravimetric loss. This can be translated into enhanced resistance to sublimation and exudation (much less volatility) compared to the prior art benzotriazole.

The instant compounds incorporated in a stabilized polymer composition would remain there during processing permitting excellent processability coupled with a final polymer pellicle with greater protection against subsequent light-induced deterioration.

EXAMPLE 33

Solubility of Benzotriazole Stabilizers

The benzotriazole stabilizers are classically materials with relatively low solubility in common organic solvents. This is particularly the case where the benzotriazole is substituted in the 2-phenyl ring with aralkyl groups intended to decrease stabilizer volatility during processing and use.

It has now been found that surprisingly substitution of the benzo ring of the benzotriazole stabilizer with an aralkyl group, such as alpha-cumyl, does not reduce solubility, but actually enhances solubility especially when the 2-phenyl ring is substituted with two alkyl groups.

Solubility data are given in the table below.

| | Solubility of Benzotriazole Stabilizer in grams per 100 grams solvent at 25° C. | | | |
|---|---|---|---|---|
| | Heptane | Xylene | Methyl Amyl Ketone | Butyl Cellosolve Acetate |
| Stabilizer* | | | | |
| B | 23 | 70 | 34 | 19 |
| F | 1.5 | 16 | 6 | 14 |
| G | 9.7 | 82 | 33 | 19 |
| of Example | | | | |
| 7 | 97 | 197 | 128 | 61 |
| 23 | >100 | >100 | >100 | >100 |

*The identities of stabilizers B, F and G are given in Example 32.

The only difference between the benzotriazole stabilizer B and that of Example 23 is in the substitution of the instant compound by an alpha-cumyl group at the 5-position in the benzo ring of the 2H-benzotriazole.

EXAMPLE 34

Absorbance at 340 nm

The compounds of this invention show unanticipated enhancement of absorbance at 340nm as can be seen from a comparison of molar extinction coefficients E compared to state of the art compound F which lacks an aralkyl-substituent in the 5-position. In many cases the enhanced absorbance is also seen when products are compared i.e. in terms of Specific Extinction Coefficient a on an equal weight rather than molar basis.

| | Enhanced Absorbance | |
|---|---|---|
| | E | a |
| Compound F | 15100 | 34 |
| Compound of | | |
| Example 7 | 19000 | 43 |
| Example 21 | 19500 | 28 |
| Example 22 | 18500 | 33 |
| Example 23 | 19100 | 41 |
| Example 24 | 17400 | 31 |
| Example 26 | 18500 | 35 |

Molar Extinction Coefficient $E = a \times$ molecular weight

Specific Extinction Coefficient $a = \dfrac{\text{absorbance}}{\text{path length (cm)} \times \text{concentration (gm/liter)}}$

EXAMPLE 35

A high solids thermosetting acrylic enamel consisting of 70 parts by weight of a copolymer prepared from methyl methacrylate, hydroxyethyl methacrylate, butyl acrylate and styrene and 30 parts by weight of hexakis-methoxymethyl melamine as crosslinker and 0.1 parts by weight of p-toluene sulfonic acid is formulate with two parts by weight of the following additives. The resulting clear enamel is then sprayed as a clear coat onto steel panels precoated with silver metallic paint.

The panels after curing are then exposed outdoors in Florida for a period of 12 months The retention of gloss is then determined:

| | % Retention of Original Gloss |
|---|---|
| Stabilizer | |
| Without Stabilizer | 30 |
| Compound F | 79 |

| | % Retention of Original Gloss |
|---|---|
| Compound of | |
| Example 22 | 73 |
| Example 23 | 76 |
| Example 24 | 82 |

EXAMPLE 36

Similar panels are those prepared in Example 35 are also exposed to ultraviolet light and humidity in the QUV apparatus for a period of 876 hours. The retention of original gloss after exposure is determined.

| | % Retention of Original Gloss |
|---|---|
| Stabilizer | |
| Compound B | 73 |
| Compound F | 60 |
| Compound G | 67 |
| Compound of | |
| Example 7 | 71 |
| Example 25 | 46 |
| Example 26 | 77 |

The data obtained in Examples 35 and 36 clearly show that the instant 2H-benzotriazole compounds, possessing the far superior solubility in most organic solvents, are essentially equally as effective as prior art benzotriazoles in terms of light stabilization efficacy.

EXAMPLE 37

Samples of light stabilizers are incorporated into polycarbonate resin by milling at 400° F. (240° C.) for a 15 minute period. During this milling period some light stabilizer is lost by sublimation depending on its volatility and compatibility. At the end of the milling period the percent stabilizer loss is determined spectrophotometrically.

| | % loss (by weight) |
|---|---|
| Stabilizer D | 40 |
| Stabilizer F | <3 |
| Stabilizer of Example 7 | <3 |
| Stabilizer of Example 21 | <3 |

What is claimed is:

1. A compound of the formula

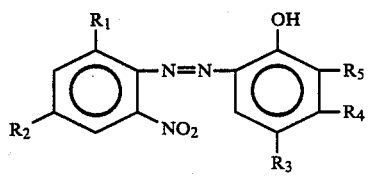

wherein
R$_1$ and R$_2$ are independently hydrogen, halogen, alkyl of 1 to 18 carbon atoms or a group of formula II

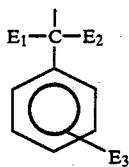 (II)

wherein $E_1$ and $E_2$ are independently hydrogen or alkyl of 1 to 4 carbon atoms and $E_3$ is hydrogen, halogen or alkyl of 1 to 4 carbon atoms, with the proviso that at least one of $R_1$ and $R_2$ must be a group of formula II;

$R_3$ is hydrogen, hydroxyl, alkyl of 1 to 12 carbon atoms, alkoxy of 1 to 4 carbon atoms, phenyl, phenyl substituted by one, two or three alkyl groups having 1 to 8 carbon atoms, cycloalkyl of 5 to 6 carbon atoms, carboalkoxy of 2 to 9 carbon atoms, chlorine, carboxyethyl or a group of formula II, $R_4$ is hydrogen, alkyl of 1 to 4 carbon atoms, alkoxy of 1 to 12 carbon atoms, chlorine or hydroxyl, and $R_5$ is hydrogen, hydroxyl, alkyl of 1 to 12 carbon atoms, chlorine, cycloalkyl of 5 to 6 carbon atoms or a group of formula II, with the proviso that $R_3$, $R_4$ and $R_5$ cannot each be hydrogen at the same time, and that only one of $R_3$, $R_4$ and $R_5$ can be hydroxyl at the same time.

2. The compound according to claim 1 which is 4-alpha, alpha-dimethylbenzyl-2-nitro-2'-hydroxy-3',5'-di-tertbutylazobenzene.

3. The compound according to claim 1 which is 4-alpha, alpha-dimethylbenzyl-2nitro-2'-hydroxy-3',5'-di-(alpha, alpha-dimethylbenzyl)-azobenzene.

4. The compound according to claim 1 which is 4-alpha, alpha-dimethylbenzyl-2-nitro-2'-hydroxy-3'-alpha, alpha-dimethylbenzyl-5-tert-octylazobenzene.

5. The compound according to claim 1 which is 4-alpha, alpha-dimethylbenzyl-2-nitro-2'-hydroxy-3',5'-di-tert-amylazobenzene.

6. The compound according to claim 1 which is 4-alpha, alpha-dimethylbenzyl-2-nitro-2'-hydroxy-3',5'-di-tert-octylazobenzene.

7. The compound according to claim 1 which is 4-alpha-methylbenzyl-2-nitro-2'-hydroxy-3',5'-di-(alpha, alpha-dimethylbenzyl)-azobenzene.

8. The compound according to claim 1 which is 4-benzyl-2-nitro-2'-hydroxy-3',5'-di-(alpha,alpha-dimethylbenzyl)-azobenzene.

* * * * *